US005834456A

United States Patent [19]
Kiefer et al.

[11] Patent Number: 5,834,456
[45] Date of Patent: Nov. 10, 1998

[54] POLYAZAMACROCYCLOFLUOROMONO-ALKYLPHOSPHONIC ACIDS, AND THEIR COMPLEXES, FOR USE AS CONTRAST AGENTS

[75] Inventors: Garry E. Kiefer, Lake Jackson; A. Dean Sherry, Dallas, both of Tex.

[73] Assignees: The Dow Chemical Company, Midland, Mich.; The University of Texas, Austin, Tex.

[21] Appl. No.: 606,162

[22] Filed: Feb. 23, 1996

[51] Int. Cl.$^6$ .......................... A61K 43/00; A61K 31/55; G01N 24/08; C07F 5/00

[52] U.S. Cl. .......................... 514/186; 540/474; 540/476; 540/477; 534/14; 534/15; 424/1.89; 424/9.3; 514/185

[58] Field of Search .................... 540/476, 465, 540/474, 477; 514/186, 185; 424/1.89, 9.3; 534/14, 15

[56] References Cited

U.S. PATENT DOCUMENTS

| | | | |
|---|---|---|---|
| 4,639,364 | 1/1987 | Hoey | 424/9 |
| 4,719,313 | 1/1988 | Gerhart et al. | 564/510 |
| 4,778,926 | 10/1988 | Gerhart et al. | 564/510 |
| 4,851,448 | 7/1989 | Gerhart et al. | 514/672 |
| 4,914,240 | 4/1990 | Gerhart et al. | 564/478 |
| 4,916,214 | 4/1990 | Chiu et al. | 534/14 |
| 5,059,412 | 10/1991 | Simon et al. | 424/1.1 |
| 5,064,633 | 11/1991 | Simon et al. | 424/1.1 |
| 5,188,816 | 2/1993 | Sherry et al. | 424/9 |
| 5,236,695 | 8/1993 | Winchell et al. | 424/9 |
| 5,247,075 | 9/1993 | Parker et al. | 540/465 |
| 5,248,498 | 9/1993 | Neumann et al. | 424/9 |
| 5,284,647 | 2/1994 | Niedballa et al. | 514/185 |
| 5,368,839 | 11/1994 | Aime et al. | 424/9 |
| 5,385,893 | 1/1995 | Keifer | 514/80 |
| 5,386,028 | 1/1995 | Tilstam et al. | 540/474 |
| 5,410,043 | 4/1995 | Platzek et al. | 540/465 |

FOREIGN PATENT DOCUMENTS

| | | | |
|---|---|---|---|
| 305320 | 8/1987 | European Pat. Off. | A61K 31/55 |
| 382582 | 8/1990 | European Pat. Off. | C07F 9/6524 |
| 455380 | 11/1991 | European Pat. Off. | A61K 49/00 |
| 468634 | 1/1992 | European Pat. Off. | A61K 49/00 |
| 592306 | 4/1994 | European Pat. Off. | A61K 49/00 |
| 628316 | 12/1994 | European Pat. Off. | A61K 49/00 |
| 8808422 | 4/1987 | WIPO | A61K 47/49 |
| 9107911 | 11/1989 | WIPO | A61B 5/05 |
| 9318795 | 3/1992 | WIPO | A61K 49/00 |
| 9311802 | 6/1993 | WIPO | A61K 49/04 |
| 9312097 | 6/1993 | WIPO | C07D 257/02 |
| 9403210 | 2/1994 | WIPO | A61K 49/00 |
| 9426726 | 11/1994 | WIPO | C07D 265/00 |
| 9427644 | 12/1994 | WIPO | A61K 49/00 |
| 9427978 | 12/1994 | WIPO | C07D 257/02 |
| 9514726 | 6/1995 | WIPO | C08G 73/00 |
| 9517910 | 7/1995 | WIPO | Q61K 49/00 |

OTHER PUBLICATIONS

G.M. Barrow, *Physical Chemistry*, 3rd Ed., McGraw–Hill, NY (1973).

J. Magnetic Resonance 33, 83–106 (1979).

Magnetic Resonance Annual, 231–266, Raven Press, NY (1985).

Frontiers of Biol Energetics I, 752–759 (1978).

J. Nucl.Med. 25, 506–513 (1984).

*Proc. of NMR Imaging Symp.* (Oct. 26–27, 1980).

F.A. Cotton et al., Adv. Inorg. Chem. 634–639 (1966).

O.T. DeJesus et al., J. Fluorine Chem., 65 (1–2), 73–77 (1993).

"Essentials of Nuclear Medicine", pp. 33–43, Ed. W.B. Hiadik, Gopal B. Saha and Kenneth T. Study, Pub. Williams & Wilkins (1987).

*Primary Examiner*—Matthew V. Grumbling
*Assistant Examiner*—Pavanaram K. Sripada
*Attorney, Agent, or Firm*—Karen L. Kimble

[57] ABSTRACT

Polyazamacrocyclofluoromonoalkylphosphonic acid compounds are disclosed which form inert complexes with Gd, Mn, Fe or La ions. The complexes are useful as contrast agents for diagnostic purposes.

22 Claims, 3 Drawing Sheets

POLYAZAMACROCYCLOFLUOROMONO-ALKYLPHOSPHONIC ACIDS, AND THEIR COMPLEXES, FOR USE AS CONTRAST AGENTS

FIELD OF THE INVENTION

This invention concerns ligands that are polyazamacrocyclofluoromonoalkylphosphonic acids, and their complexes, for use as contrast agents in magnetic resonance imaging (MRI). Some ligands and complexes are also useful as imaging agents for in vivo spectroscopy of fluorine. To better understand this invention, a brief background on MRI is provided in the following section.

BACKGROUND OF THE INVENTION

MRI is a non-invasive diagnostic technique which produces well resolved cross-sectional images of soft tissue within an animal body, preferably a human body. This technique is based upon the property of certain atomic nuclei (e.g., water protons) which possess a magnetic moment [as defined by mathematical equations, see G. M. Barrow, *Physical Chemistry*, 3rd Ed., McGraw-Hill, N.Y. (1973)] to align in an applied magnetic field. Once aligned, this equilibrium state can be perturbed by applying an external radio frequency (RF) pulse which causes the protons to be tilted out of alignment with the magnetic field. When the RF pulse is terminated, the nuclei return to their equilibrium state and the time required for this to occur is known as the relaxation time. The relaxation time consists of two parameters known as spin-lattice (T1) and spin-spin (T2) relaxation and it is these relaxation measurements which give information on the degree of molecular organization and interaction of protons with the surrounding environment.

Since the water content of living tissue is substantial and variations in content and environment exist among tissue types, diagnostic images of biological organisms are obtained which reflect proton density and relaxation times. The greater the differences in relaxation times (T1 and T2) of protons present in tissue being examined, the greater will be the contrast in the obtained image [*J. Magnetic Resonance* 33, 83–106 (1979)].

It is known that paramagnetic chelates possessing a symmetric electronic ground state can dramatically affect the T1 and T2 relaxation rates of juxtaposed water protons and that the effectiveness of the chelate in this regard is related, in part, to the number of unpaired electrons producing the magnetic moment [*Magnetic Resonance Annual*, 231–266, Raven Press, NY (1985)]. It has also been shown that when a paramagnetic chelate of this type is administered to a living animal, its effect on the T1 and T2 of various tissues can be directly observed in the magnetic resonance (MR) images with increased contrast being observed in the areas of chelate localization. It has therefore been proposed that stable, non-toxic paramagnetic chelates be administered to animals in order to increase the diagnostic information obtained by MRI [*Frontiers of Biol. Energetics* I, 752–759 (1978); *J. Nucl. Med.* 25, 506–513 (1984); *Proc. of NMR Imaging Symp.* (Oct. 26–27, 1980); F. A. Cotton et al., *Adv. Inorg. Chem.* 634–639 (1966)]. Paramagnetic metal chelates used in this manner are referred to as contrast enhancement agents or contrast agents. Therefore, over the past decade the use of stable, non-toxic paramagnetic chelates in conjunction with MRI examinations has become increasingly important for enhancing the accuracy of clinical diagnoses.

There are a number of paramagnetic metal ions which can be considered when undertaking the design of an MRI contrast agent. In practice, however, the most useful paramagnetic metal ions are gadolinium ($Gd^{+3}$), iron ($Fe^{+3}$), manganese ($Mn^{+2}$) and ($Mn^{+3}$), and chromium ($Cr^{+3}$), because these ions exert the greatest effect on water protons by virtue of their large magnetic moments. In a non-complexed form (e.g., $GdCl_3$), these metal ions are toxic to an animal, thereby precluding their use in the simple salt form. Therefore, a fundamental role of the organic chelating agent (also referred to as a ligand) is to render the paramagnetic metal non-toxic to the animal while preserving its desirable influence on T1 and T2 relaxation rates of the surrounding water protons.

At the present time, the only commercial contrast agents available in the U.S. are the complex of gadolinium with diethylenetriaminepentaacetic acid ($DTPA-Gd^{+3}$— MAGNEVIST™ by Schering AG) and a DO3A derivative [1,4,7-tris(carboxymethyl)-10-(2-hydroxypropyl)-1,4,7,10-tetraazacyclododecanato]gadolinium (PROHANCE™ by Bristol Meyers Squibb). MAGNEVIST™ and PROHANCE™ are each considered as a non-specific agent or perfusion agent since they freely distribute in extracellular fluid followed by efficient elimination through the renal system. MAGNEVIST™ has proven to be extremely valuable in the diagnosis of brain lesions since the accompanying breakdown of the blood/brain barrier allows perfusion of the contrast agent into the affected regions. In addition to MAGNEVIST™, Guerbet is commercially marketing a macrocyclic perfusion agent (DOTAREM™) which presently is only available in Europe. PROHANCE™ is shown to have fewer side effects than MAGNEVIST™. A number of other potential contrast agents are in various stages of development.

Ongoing MRI research and in vivo spectroscopy is investigating other NMR active nuclides such as $^{13}C$, $^{31}P$, $^{19}F$ and $^{23}Na$. However, when the isotope natural abundance and sensitivity are taken into account, only $^{19}F$ and $^{31}P$ offer any potential for imaging with current hardware technology. Additionally, $^{19}F$ could be adapted to existing imaging systems because: it has a natural abundance of 100%; a sensitivity which is 83% that of $^1H$; and resonates at a frequency close to $^1H$. Since $^{19}F$ is not native to living tissue, it can be imaged directly without any background contrast. This feature, coupled with favorable imaging characteristics of $^{19}F$, offers the potential for detecting the presence of contrast agent at extremely low concentrations. In addition, the sensitivity can be further augmented by incorporating a multiplicity of magnetically equivalent $^{19}F$ nuclei into the contrast agent.

The use of fluorine in imaging is not currently commercially practiced nor very prevalent in the art. There is also only limited art suggesting the use of cyclic organofluorine derivatives for spectroscopic applications. This summary is provided only as a review of this area, and is not intended as exhaustive. O. T. DeJesus et al., *J. Fluorine Chem.*, 65(1–2), 73–77 (1993) describe the synthesis of fluoro-α-fluoromethyl-p-tyrosine as a potential imaging agent for dopamine neurons. European 0 592 306 A2 describes a $^{19}F$ MRI contrast medium having a metal complex compound in which a polyamine possessing at least one fluorine atom is coordinate-bonded to a paramagnetic metal. WO 9318795 discloses a stated stable MRI contrast medium having a particulate paramagnetic compound which may be dispersed in a 1–12 carbon perfluoro compound. WO 9403210 discloses a contrast agent having a polymer containing 1 or 2 different NMR visible nuclei with an example of a fluorinated organosilicon polymer. U.S. Pat. No. 5,284,647 describes a mesotetraphenylporphyrin complex that can contain fluorine. U.S. Pat. No. 5,248,498 discloses perfluorinated fullerene compositions.

SUMMARY OF THE INVENTION

Surprisingly, it has now been found by the present invention that various polyazamacrocyclofluoromonoalkylphosphonic acid ligands, as their complexes, can be used as contrast agents. These paramagnetic chelates provide a duality of function by acting as a $^{1}$H proton imaging contrast agent and are directly observable through the presence of the NMR active $^{19}$F nucleus to enable in vivo spectroscopy and the potential for $^{19}$F imaging. In addition, the incorporation of the fluorine nucleus into an organic ligand provides a method for modification of lipophilic character which is valuable in the design of tissue specific contrast agents.

Furthermore, these ligands may have their charge modified, i.e. by the substitution of the ligand and metal selected, which can effect their ability to be more site specific.

Specifically, the present invention concerns ligands that are polyazamacrocyclofluoromonoalkylphosphonic acid compounds of the general formula wherein:

R is hydrogen or where:
m is 0 or an integer of 1 through 4;
n is an integer of 1, 2 or 3;
R$^{1}$ and R$^{1}$ are independently hydrogen or fluoro atom;
with the proviso that at least one R must be other than hydrogen;
Z is a group of the formula where R is defined as before;
q is an integer of 1 or 2;
y is an integer of 1, 2 or 3;
x is 0 or 1;
with the proviso that when y is 1, x is 1 and when y is 3, x is 0; or
pharmaceutically-acceptable salts thereof.

Examples of ligands that are within the scope of Formula (I) are polyazamacrocyclofluoromonoalkylphosphonic acid compounds of any one of the formula (II)

(III)

(IV)

(V)

(VI)

wherein:
R is hydrogen or where:
m is 0 or an integer of 1 through 4;
n is an integer of 1, 2 or 3;
R$^{1}$ and R$^{1}$ are independently hydrogen or fluoro atom;
with the proviso that at least one R must be other than hydrogen; or
pharmaceutically-acceptable salts thereof.

Particularly preferred are those ligands where all R terms present are substituted with the fluoro containing group.

More preferred are those ligands of any of the above formulae where m is 0 or 1 and n is 1.

The ligands of Formula (I) may be complexed with various metal ions, such as gadolinium ($Gd^{+3}$), iron ($Fe^{+3}$), manganese ($Mn^{+3}$) and chromium ($Cr^{+3}$), with $Gd^{+3}$ being preferred. Such complexes are useful as MR contrast agents.

Because the present invention uses $^{19}F$ for NMR imaging, both the fluorine and proton images are desired. The desired metals for such a combined image, either by using a single complex or a mixture of two or more complexes employs the lanthanide series of metals, particularly, lanthanum ($La^{+3}$), cerium ($Ce^{+3}$), praseodymium ($Pr^{+3}$), neodymium ($Nd^{+3}$), promethium ($Pm^{+3}$), samarium ($Sm^{+3}$), europium ($Eu^{+3}$), terbium ($Tb^{+3}$), dysprosium ($Dy^{+3}$), holmium ($Ho^{+3}$), erbium ($Er^{+3}$), thulium ($Tm^{+3}$), ytterbium ($Yb^{+3}$), and lutetium ($Lu^{+3}$) with $La^{+3}$ being preferred.

Both the ligand and complexes may be formulated to be in a pharmaceutically acceptable form for administration to an animal.

DETAILED DESCRIPTION OF THE INVENTION

The compounds of Formulae (II)–(VI) are numbered for nomenclature purposes as follows:

(II)

(III)

(IV)

One aspect of the present invention concerns development of contrast agents having synthetic modifications to the paramagnetic chelate, enabling site specific delivery of the contrast agent to a desired tissue. The advantage of the site specificity being increased contrast in the areas of interest based upon tissue affinity, as opposed to contrast arising from non-specific perfusion which may or may not be apparent with an extracellular agent.

Unexpectedly, however, it has been found that with the fluorinated compounds of the present invention, even though the lipophilicity is not as great as the corresponding alkoxy compounds [as measured by the standard octanol/water coefficient method, see for example, "Essentials of Nuclear Medicine", pp 33–43, Ed. W. B. Hiadik, Gopal B. Saha and Kenneth T. Study, Pub. Williams & Wilkins (1987)], the present compounds are still liver and gastrointestinal (GI) tract contrast agents.

As used herein, "complex" refers to a complex of the compound of the invention, e.g. Formulae (I)–(VI), complexed with a paramagnetic metal ion or lanthanide series ion, where at least one metal atom is chelated or sequestered.

As used herein, "pharmaceutically-acceptable salts" means any salt or mixtures of salts of a compound of Formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) where the salt is potassium or sodium. Also included are mixtures of the above salts.

The formulations of the present invention are in liquid form containing the complex. These formulations may be in kit form such that the two components are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the free base. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50% of the organic solvent by volume.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethlycellulose. Suitable physiologically acceptable adjuvants, if necessary to keep the complex in suspension, may be chosen from among thickners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters.

Many substances which effect the hydrophobicity, density, and surface tension of the liquid suspension medium can assist in making injectable suspensions in individual cases. For example, silcone antifomes, sorbitol, and sugars are all useful suspending agents.

The formulations of the present invention are administered in an effective amount to an animial for the diagnosis of a disease state in the animal. The "effective amount" of the formulation to administer to the animal is from about 0.001 to 0.2 mmol/Kg. The diease state is frequently from cancer.

DETAILED DESCRIPTION OF THE PROCESS

The compounds of Formula (I) are prepared by various processes. The starting material ligands to make the polyazamacrocyclofluoromonoalkylphosphonic acids compounds of this invention have been described in earlier patent applications as follows.

Discussion of suitable processes to make the starting ligands for compounds of Formula (II) are disclosed in published WO 94/26753 and copending U.S. patent application Ser. No. 065,963, filed May 6, 1993, entitled "Process for the Preparation of Azamacrocyclic or Acyclic Aminophosphonate Ester Derivatives" by G. E. Kiefer (Attorney Docket No. C-41,184), the disclosure of which is hereby incorporated by reference; and in published WO 95/14726 and in copending U.S. patent application Ser. No. 320,620, filed Oct. 7, 1994, entitled "Process for Preparing Polyazamacrocycles" by P. S. Athey and G. E. Kiefer (Attorney Docket No. C-41,033A), the disclosure of which is hereby incorporated by reference.

Discussion of suitable processes to make the starting ligands for compounds of Formula (III) are disclosed in published WO 93/11802 and in our copending U.S. patent application Ser. No. 058,101, filed May 6, 1993, entitled "Bicyclopolyazamacrocyclophosphonic Acids, and Complexes and Conjugates Thereof, for Use as Contrast Agents" by G. E. Kiefer, et al. (Attorney Docket No. C-38,662B), the disclosure of which is hereby incorporated by reference.

Discussion of suitable processes to make the starting ligands for compounds of Formulae (IV) and (V) are disclosed in published WO 94/26726 and in U.S. Pat. No. 5,385,893, issued Jan. 31, 1995, entitled "Tricyclopolyazamacrocyclophosphonic Acids, Complexes and Derivatives Thereof, for Use as Contrast Agents" by G. E. Kiefer (Attorney Docket No. C-40,856), the disclosure of which is hereby incorporated by reference.

Discussion of suitable processes to make the starting ligands for compounds of Formula (VI) are in disclosed in published WO 92/08725 and in U.S. Pat. No. 5,385,893, entitled "Polyazamacrocyclic Compounds for Complexation of Metal Ions" by A. Dean Sherry et al., the disclosure of which is hereby incorporated by reference.

Typical general synthetic approaches to such processes to make the final ligands of the present invention are provided by the reaction schemes given below.

In the following Schemes, the metal ion (M) may be any of the ones listed before for the complexes of this invention; Gd and La shown. The ligand of Formula (I) can be used in these schemes, but for illustration a given scheme is shown using one of the ligands of Formula (II)–(VI).

In Scheme 1, the compounds of Formula (II) are prepared wherein all four R terms are other than hydrogen; n=1 (but would also apply if n=2 or 3 with the corresponding change in the reagent), m=0 (but would also apply if m=1–4 with the corresponding change in the reagent).

Scheme 1

-continued
Scheme 1

Scheme 2 prepares the compounds of Formula (III) wherein all three R terms are other than hydrogen; n=1 (but would also apply if n=2 or 3 with the corresponding change in the reagent), m=0 (but would also apply if m=1–4 with the corresponding change in the reagent.

Scheme 3 prepares the compounds of Formula (IV) wherein both R terms are other than hydrogen; n=1 (but would also apply if n=2 or 3 with the corresponding change in the reagent), m=0 (but would also apply if m=1–4 with the corresponding change in the reagent.

Scheme 2

Scheme 3 a complex of
Formulae (I)
and (IV)

a compound of
Formulae (I)
and (IV)

Scheme 4 prepares the compounds of Formula (V) wherein all three R terms are other than hydrogen; n=1 (but would also apply if n=2 or 3 with the corresponding change in the reagent), m=0 (but would also apply if m=1–4 with the corresponding change in the reagent.

Scheme 5 prepares the compounds of Formula (VI) wherein all three R terms are other than hydrogen; n=1 (but would also apply if n=2 or 3 with the corresponding change in the reagent), m=0 (but would also apply if m=1–4 with the corresponding change in the reagent.

phonate ester moiety via the condensation of the secondary nitrogen with paraformaldehyde. The phosphonate ester is then subjected to nucleophilic attack by tris(2,2,2-trifluoroethyl)phosphite and elimination of 1 equivalent of trifluoroethanol to yield (about 100%) a corresponding Scheme 5

In the Schemes 1–5 above, for the full esters of the ligand formed, e.g. $P(O)(OCH_2CF_3)_2$, pressure is not critical so that ambient pressure is used. As the reaction is exothermic, the temperature is controlled to be maintained below 40° C. during the first hour; and after the first hour, the temperature can be raised to facilate completion of the reaction but need not exceed about 90° C. The pH of the reaction is not critical and the reaction is run in the presence of a non-aqueous liquid, such as the trialkyl phosphite reagent or a solvent. A solvent is preferrably used; examples of such solvents are:

aprotic polar solvents such as tetrahyrdofuran (THF), 1,4-dioxane, acetonitrile, and other similar inert, non-aqueous solvents; and alcohols where the alkyl portion is the same as the R obtained, such as methanol, ethanol and propanol.

THF is the preferred solvent. The order of addition of the reactants and the azamacrocyclic or acyclic aminophosphonate starting material is not critical.

All the ligands of Formulae (I)–(VI) wherein the half esters are prepared, e.g. $PO_2(OCH_2CF_3)$, by aqueous base hydrolysis (KOH is shown) is accomplished after the formation of the corresponding full ester. Examples of suitable bases are alkali metal hydroxides, e.g. sodium or potassium hydroxide. The amount of base used is from about 1–10 equivalents per secondary amine. As the alkyl chain length of the m term is higher, then a cosolvent is used with the water. Suitable examples of such cosolvents are organic water missible solvent, such as 1,4-dioxane, THF and acetone.

In these methods to prepare the ligands of the present invention, the corresponding polyazamacrocyclomonoalkylphosphonic acid is functionalized to include at least one fluorine atom. The process, as illustrated above, begins by reacting the unsubstituted polyazamacrocyclic ring desired with $P(OR)_3$, where R is the desired $C_1$–$C_4$ alkyl, with $CH_2O$ in THF (or suitable inert solvent) at about 25° C. (ambient temperature). This reaction incorporates the phosdialkylphosphonate ester. This product is then hydrolyzed under basic conditions to give the corresponding monophosphonic acid having multiple $^{19}F$ nuclei. (e.g., When Cyclen, 1,4,7,10-tetraazacyclododecane is used in this process, a final product is [DOTP(F)ME] which has 12 equivalents of $^{19}F$ nuclei contributing to the overall fluorine signal intensity.)

Theory of the Invention

While not wishing to be bound by theory, it is believed that the advantageous results of the present invention are obtained because the inherent sensitivity of $^{19}F$ may also permit detection of subtle changes in fluorine chemical shift as a function of environment, thus revealing insight into physiological and metabolic processes. In theory, the resulting contrast agent possessing an $^{19}F$ nucleus and a paramagnetic ion could be used to generate both proton and fluorine images during a single MR examination. The resulting composite image produced ($^{19}F/^{1}H$) would reveal significantly more information about soft tissue morphology and condition.

The invention will be further clarified by a consideration of the following examples, which are intended to be purely exemplary of the present invention.

General Materials and Methods.

All reagents were obtained from commercial suppliers and used as received without further purification. NMR spectra were recorded on a Bruker AC-250 MHz spectrometer equipped with a multi-nuclear quad probe ($^{1}H$, $^{13}C$, $^{31}P$, and $^{19}F$) at 297° K. unless otherwise indicated. $^{1}H$ spectra were recorded by employing solvent suppression pulse sequence ("PRESAT", homo-nuclear presaturation). $^{1}H$ spectra are referenced to residual chloroform (in $CDCl_3$) at $\delta 7.26$ or extemally referenced to dioxane (in $D_2O$) at $\delta 3.55$. $^{13}C$, $^{31}P$ and $^{19}F$ spectra reported are broad band proton decoupled unless otherwise specified. Assignments of $^{13}C$ {$^{1}H$} chemical shifts were aided by Distortionless Enhancement by Polarization Transfer (DEPT) experiments for determining carbon multiplicity. $^{13}C$ {$^{1}H$} spectra are referenced to center peak of $CDCl_3$ at δ77.00 (in $CDCl_3$) or external dioxane at δ66.66 (in $D_2O$). $^{31}P$ {$^1H$} spectra were referenced to external 85% $H_3PO_4$ at δ0.00. 19F spectra were externally referenced to trifluroacetic acid.

$^{19}F$ NMR Measurements $^{19}F$ spectra were recorded on a General Electric GN-500 (11.7 T) spectrometer in a 5 mm tube while maintaining the temperature at 25° C. A standard inversion recovery sequency was used to record the data for determination of longitudinal relaxation times. The data were measured by ensuring that a delay of at least 5 $T_1$ was allowed between successive pulse sequences to allow return of the spin system to equilibrium. $T_1$ was then evaluated using befit software provided by GE. Spin—spin relaxation times, $T_2$, were estimated from the line width ($v_{1/2}$) using the relationship: $T_2=1/\pi v_{1/2}$.

pH Stability General Procedure

A stock $^{159}GdCl_3$ (or $^{153}SmCl_3$) solution was prepared by adding 2 μL of 3×10$^{-4}$M $^{159}GdCl_3$ in 0.1N HCl to 2 mL of a 3×10$^{-4}$M $GdCl_3$ carrier solution. Appropriate ligand solutions were then prepared in deionized water. The 1:1 ligand/metal complexes were then prepared by combining the ligands (dissolved in 100–500 μL of deionized water) with 2 mL of the stock $^{159}GdCl_3$ solution, followed by through mixing to give an acidic solution (pH=2). The pH of the solution was then raised to 7.0 using 0.1N NaOH. The percent metal as a complex was then determined by passing a sample of the complex solution through a Sephadex™ G-50 column, eluting with 4:1 saline (85% NaCl/NH$_4$OH) and collecting 2×3 mL fractions. The amount of radioactivity in the combined elutions was then compared with that left on the resin (non-complexed metal is retained on the resin). The pH stability profile was generated by adjusting the pH of an aliquot of the complex solution using 1M NaOH or 1M HCl and determining the percent of the metal existing as a complex using the ion exchange method described above. The Sm results are known by expermental comparison to be identical for complexation and biodistribution of the ligands of this invention.

STARTING MATERIALS

Example A

Preparation of 2,6-bis(chloromethyl)pyridine

To 100 mL of thionyl chloride that was cooled (ice bath) was added 24 g (0.17 mol) of 2,6-bis(hydroxymethyl) pyridine. After 30 min, the reaction mixture was warmed to room temperature, then refluxed for 1.5 hrs. After cooling the reaction mixture to room temperature, the solid which formed was filtered, washed with benzene and dried in vacuo. The solid was then neutralized with saturated $NaHCO_3$, filtered and dried to yield 23.1 g (71.5%) of the titled product as an off-white crystalline solid, mp 74.5°–75.5° C., and further characterized by:

$^1H$ NMR ($CDCl_3$); δ 4.88 (s, 4H), 7.25–7.95 (m, 3H).

Example B

Preparation of 3,6,9-tris(p-tolylsulfonyl)-3,6,9,15-tetraazabicyclo[9.3.1]pentadeca-1(15),11,13-triene A DMF solution (92 mL) of 6.9 g (11.4 mmol) of 1,4,7-tris(p-tolylsulfonyl)diethylenetriamine disodium salt was stirred and heated to 100° C. under nitrogen. To the solution was added dropwise over 45 min 2 g (11.4 mmol) of 2,6-bis(chloromethyl)pyridine (prepared by the procedure of Example A) in 37 mL of DMF. When the addition was completed the reaction mixture was stirred at 40° C. for 12 hrs. To the reaction mixture was then added 50–75 mL of water, resulting in immediate dissolution of NaCl, followed by precipitation of the title product. The resulting slurry was then filtered and the solid washed with water and dried in vacuo. The title product was obtained as a light-tan powder, 6.5 g (86%), mp 168°–170° C. dec. and further characterized by:

$^1H$ NMR ($CDCl_3$); δ 2.40 (s, 3H), 2.44 (s, 6H), 2.75 (m, 4H), 3.30 (m, 4H), 4.28 (s, 4H), 7.27 (d, 2H), 7.34 (d, 4H), 7.43 (d, 2H), 7.65 (d, 4H), 7.75 (t, 1H); and $^{13}C$ NMR; δ 21.48, 47.29, 50.37, 54.86, 124.19, 127.00, 127.11, 129.73, 135.04, 135.74, 138.95, 143.42, 143.73, 155.15.

Example C

Preparation of 3,6,9,15-tetraazabicyclo[9.3.1] pentadeca-1(15),11,13-triene; starting ligand for Formula (III)

A solution of HBr and AcOH was prepared by mixing 48% HBr and glacial AcOH in a 64:35 ratio. To 112 mL of the HBr/AcOH mixture was added 5.5 g (8.2 mmol) of 3,6,9-tris(p-tolylsulfonyl)-3,6,9,15-tetraazabicyclo[9.3.1] pentadeca-1(15),11,13-triene (prepared by the procedure of Example B) and the reaction mixture was heated at mild reflux with constant stirring for 72 hrs. The reaction mixture was then cooled to room temperature and concentrated to approximately 1/10 of the original volume. The remaining solution was stirred vigorously and 15–20 mL of diethyl ether was added. A off-white solid formed which was filtered, washed with diethyl ether, and dried in vacuo. The dry tetrahydrobromide salt was then dissolved in 10 mL of water, adjusted to pH 9.5 with NaOH (50% w/w) and continuously extracted with chloroform for 4 hrs. After drying over anhydrous sodium sulfate, the chloroform was evaporated to give a light-tan oil which gradually crystallized upon standing at room temperature to yield 1.2 g (71%) of the title product, mp 86°–88° C. and further characterized by:

$^1H$ NMR ($CDCl_3$); δ 2.21 (m, 4H), 2.59 (m, 4H), 3.06 (s, 3H), 3.85 (s, 4H), 6.89 (d, 2H), 7.44 (t, 1H); and $^{13}C$ NMR; δ 48.73, 49.01, 53.63, 119.67, 136.29, 159.54.

Example D

Preparation of a cyclized intermediate

To a vigorously stirring mixture of $K_2CO_3$ (0.72 mol) in 1 L of DMF at 100° C. was added a 1.3 L DMF solution containing both 1,1'-(1,2-ethanediyl)-bis[4,5-dihydro-1H]-imidazoline (104 g, 0.63 mol) and 1,2-dibromoethane (165 g, 0.88 mol). Upon completion of the addition (~30 min), the resulting solution was heated for an additional 30 min at 100° C. After cooling to 50° C., the $K_2CO_3$ was filtered and the resulting filtrate was concentrated to dryness. The crude cyclized salt was washed with acetone to remove the trace impurities. The isolated yield of desired cyclized intermediate product was 99% (171 g, 0.62 mol) and characterized by:

$^{13}C$ NMR ($CDCl_3$); δ 162.0 (C), 72.7 (CH), 54.2 (CH$_2$), 52.4 (CH$_2$), 45.5 (CH$_2$), 44.3 (CH$_2$).

The cyclized intermediate product is represented by the formula:

Example E

Preparation of 1,4,7,10-tetraazacyclododecane, Cyclen; starting ligand for Formula (II)

The cyclized intermediate (113 g, 0.41 mol), prepared by the procedure of Example D, was dissolved in water to give a total volume of 450 mL and was added dropwise to a refluxing solution of 400 mL of NaOH (8 eq, 129 g, 3.3 mol). The solution was heated for an additional 30 min after completion of the addition of the cyclized intermediate. The aqueous caustic solution was filtered while hot and then the filtrate cooled to room temperature. The aqueous filtrate was then concentrated (rotoevaporator) until crystalline solid was observed in the solution. After cooling, Cyclen was filtered and the process was repeated on the filtrate until no further crystallization occurred. The aqueous solution was then concentrated to dryness and the remaining precipitate removed by extractions of the solid residue with hot toluene. The overall yield of (6) was 88% (62 g, 0.36 mol) and characterized by:

$^1$H NMR (CDCl$_3$); δ 2.54;

$^{13}$C NMR (CDCl$_3$); δ 45.9; and

Mass Spec; m/e 173 (M+1), 173 (2), 128 (8), 104 (45), 85 (100), 56 (80).

Example F

Preparation of N,N'-ditosyl-2,11-diaza[3.3]-(2,6) pyridinophane

To a stirred solution of tosylamide, sodium salt (TsNHNa), (13.52 g, 70 mmol) in anhydrous DMF (1.3 L) at 80° C. was added dropwise (1.5 hr) under a N$_2$ atmosphere a solution of 2,6-bis(chloromethyl)pyridine (12.32 g, 70 mmol) in DMF (200 mL). After 1 hr, solid TsNHNa (13.52 g, 70 mmol) was added all at once, and the mixture was stirred at 80° C. for additional 16 hr. The reaction mixture was then cooled to room temperature and decanted. The solvent was removed in vacuo and the resulting residue was combined with acetone and filtered to give a waxy solid which was continuously extracted (Soxlet) with acetone (300 mL) for 48 hr. The product was isolated as the precipitate at the bottom of the heating flask. Upon drying, the product was isolated as white powder (5.24 g, 27%): mp=246°–248° C. and further characterized by:

$^1$H NMR (DMSO-d6); δ 2.42 (s, 6H), 4.38 (s, 8H), 6.99 (d, 4H), 7.40–7.49 (m, 6H), 7.88 (d, 4H); and $^{13}$C {$^1$H} NMR (DMSO-d6); δ 20.91, 55.55, 122.12, 126.92, 129.88, 135.99, 137.03, 143.30, 154.71; and is illustrated by the formula

Example G

Preparation of 2,11-diaza[3.3](2,6)pyridinophane; a starting ligand of Formula (IV)

N,N'-ditosyl-2,11-diaza[3.3](2,6)pyridinophane (5.24 g, 9.5 mmol), prepared in Example F, was dissolved in 90% H$_2$SO$_4$ (48 mL) and heated at 110° C. with stirring for 2 hr. After the solution was cooled to room temperature, it was slowly diluted with deionized water (50 mL) while chilling in an ice bath. The resulting solution was then poured into a 25% NaOH solution (200 mL) which was cooled in an ice bath. The resulting white solid was extracted with CHCl$_3$ (3×100 mL), dried over anhydrous MgSO$_4$, filtered, and concentrated in vacuo to dryness to give the titled product as a waxy white solid (1.69 g, 74%) and further characterized by:

$^1$H NMR (CDCl$_3$); δ 3.91 (s, 8 H), 6.47 (d, 4H), 7.06 (t, 2H); and $^{13}$C {$^1$H} NMR (CDCl$_3$); δ 55.89, 119.73, 135.71, 159.36;

CG/mass spectra m/z M$^+$ 240; and is illustrated by the formula

Example H

Preparation of N,N',N"-tritosyl-2,11,20-triaza[3.3.3] (2,6)pyridinophane

Isolated as a by-product from the reaction used for preparation of N,N'-ditosyl-2,11-diaza[3.3]-(2,6) pyridinophane, prepared in Example F, (remaining part on the extractor thimble after Soxlet extraction) mp 260°–262° C.; and further characterized by:

$^1$H NMR (DMSO-d6); δ 2.31 (s, 9H), 4.08 (s, 12H), 7.01 (d, 4H), 7.30 (d, 6H), 7.52 (t, 3H), 7.67 (d, 6H); and $^{13}$C {$^1$H} NMR (DMSO-d6); δ 20.92, 54.03, 120.55, 127.13, 129.83, 135.12, 136.83, 143.45, 155.47; and is illustrated by the formula:

Example I

Preparation of 2,11,20-triaza[3.3.3](2,6) pyridinophane; starting ligand for Formula (V)

N,N',N"-tritosyl-2,11,20-triaza[3.3.3]-(2,6)pyridinophane (0.5 g, 0.61 mmol), prepared in Example H was dissolved in 90% $H_2SO_4$ (6 mL) and heated at 110° C. with stirring for 2 hr. The solution was then cooled to room temperature and slowly diluted with deionized water (6 mL) while chilling in a ice bath. The resulting solution was then poured into a 25% NaOH solution (22 ml) which was cold in an ice bath. The resulting white solid was extracted with $CHCl_3$ (2×30 mL), dried over anhydrous $MgSO_4$, filtered, and concentrated in vacuo to dryness to give the titled product as a waxy white solid (0.167 g, 76%); and further characterized by:

$^1$H NMR ($CDCl_3$); δ 3.03 (s, 3H), 3.93 (s, 12H), 7.08 (d, 6H), 7.54 (t, 3H); and $^{13}$C {$^1$H} NMR ($CDCl_3$); δ 54.58, 120.72, 136.50, 158.64;

GC/mass spectra m/z $M^+$ 360; and is illustrated by the formula:

Example J

Preparation of 1,4,7-triazacyclononane trihydrobromide

A: Preparation of N,N',N"-tri(p-tolunensulfonyl)-diethylene triamine

A solution of 191 g of p-tolunensulfonyl chloride in 500 mL of ether was added dropwise to a solution of 38 mL of diethylene triamine and 40 g of sodium hydroxide in 250 mL of water. The mixture was stirred for one hour at room temperature. A white precipate was formed and collected by filtration, washed with water, and recrystalized using methanol. (Acetonitrile could also be used.) The melting point of the recrystallized precipitate was 174° to 175° C. The uield was 90% (and should always be above 70%).

B: Preparation of di(p-tolunensulfonyl)ethylene glycol

Ethylene glycol (28 mL) and 100 mL of pyridine were added over a 2.5 hour period to a stirred mixture of 210 g of tosyl chloride in 225 mL of pyridine, with the mixture being cooled by a water bath. After stirring for several hours, the mixture was shaken with one liter of ice water for about 10 min and then filtered. The residue was washed with ether, dilute sulfuric acid, water and finally ether. (Each of the washed liquids was ice cold.) The residue was then dried by vacuum pumping and recrystallized from boiling acetonitrile. The recrystallized residue, yield 75%, had a melting point of 123° to 125° C.

C: Preparation of the disodium salt of N,N',N"-tri(p-tolunensulfonyl)diethylene triamine Each part of this step was conducted under a nitrogen atmosphere. Sodium metal (2.65 g) was weighed in hexane and placed in about 75 mL of pure ethanol. The sodium-ethanol reaction is highly exothermic, and the heat helps dissolve the sodium to give sodium ethoxide. A hot slurry of 28.3 g of 1,4,7-tritosyl-1,4,7-triazaheptane from Step A and 150 mL of ethanol was stirred in a reaction vessel with a reflux condenser. The slurry was heated to reflux using an oil bath, and then the sodium ethoxide was added as rapidly as possible. After continued stirring and flushing with nitrogens a white solid percipitated. Slight heating and flushing continued until all ethanol was removed and a residue of dry disodium salt of 1,4,7-tritosyl-1,4,7-triazaheptane remained.

D: Synthesis of 1,4,7-triazacyclononane-N,N',N"-tritosylate

This step was conducted without removing the dry salt from Step C reaction vessel. The residue salt from Step C was dissolved in 225 mL of dry dimethyl formamide (DMF), again under a nitrogen atmosphere. The mixture was stirred and heated to 95° to 110° C. Next, a 0.2M solution of 18.5 g of ethylene glycolditosylate in DMF was added over a period of three hours. After one additional hour of stirring at 100° C., the mixture was cooled overnight. It was then concentrated by distillation under reduced pressure until precipitation began. The concentrate was poured into 500 mL of vigorously stirred water and filtered. The residue was washed with water, dried by vacuum pumping, and recrystallized from boiling acetone. The product had a melting point of 217° to 220° C. and was present in a yield of 70%.

E: Synthesis of 1,4,7-triazacyclononane trihydrobromide

A mixture of 120 mL of 47% HBr, 67 mL of glacial acetic acid, and 13.99 g of the product of Step D were heated to 100° C., and the volume was then remeasured. The mixture was then refluxed for fifty hours and concentrated by atmospheric distillation to about 20% of the beginning volume. The concentrate was then filtered. The residue, containing 1,4,7-triazacyclononane-N,N',N"-trihydrobromide was extracted into water and then recovered by evaporation in vacuo. The trihydrobromide was recrystallized from boiling hydrobromic acid. Its melting point was 280° C., and it was present in 70% yield. Tosylate groups were completely absent in the NMR spectra of the trihydrobromide.

FINAL PRODUCTS

LIGAND

Example 1

Preparation of 1,4,7,10-tetraazacyclododecane-1,4,7,10-tetra(methylenephosphonate bistrifluoroethyl ester); [DOTPbis(F)ME]; a ligand of Formula (II)

To a THF (70 mL) suspension of 10 g (58 mmol) of 1,4,7,10-tetraazacyclododecane, prepared by the procedure of Example E, and 7.4 g (246 mmol) of paraformaldehyde was added. The solution was cooled in an ice bath and 81 g (246 mmol) of tris(2,2,2-trifluoroethyl)phosphite was added in one portion. The solution was then allowed to warm to room temperature, and stirred for 24 hrs under a $N_2$ atmosphere at 25° C. The reaction was then concentrated in vacuo to give a viscous orange oil. This may be used without purification.

When desired, the oil was then dissolved in 50 mL of acetone and passed through an alumina column (basic form) eluting with acetone. Upon concentration of the acetone eluent, the perester was obtained as a viscous, moisture sensitive, orange oil, yield 60 g (86%) and was used in sebsequent reactions without further purification.

Example 2

Preparation of 1,4,7,10-tetraazacyclododecane-1,4,7, 10-tetra(methylenephosphonate monotrifluoroethyl ester) tetrapotassium salt; [DOTP(F)ME]; a ligand of Formula (II)

To an aqueous dioxane solution (100 mL $H_2O$/70 mL dioxane) was added 25 g (0.45 mol) of KOH along with 60 g (50 mmol) of the perester prepared in Example 1. The solution was then stirred at reflux for 1 hr and cooled to room temperature. Upon concentration of the aqueous reaction mixture the desired title product precipitated as an off-white solid and was filtered to yield 15 g (15 mmol, 30%) and further characterized by:

$^{13}C$ NMR ($D_2O$); δ 52.95 (d), 53.88 (s), 63.60 (qd), 126.49 (qd); and $^{31}P$ NMR ($D_2O$); δ 22.69; and $^{19}F$ NMR ($D_2O$); δ 3.51.

Example 3

Preparation of 1,4,7,10-tetraazacyclododecane-1,4,7, 10-tetra(methylenephosphonate monotrifluoroethyl ester) free acid; DOTP(F)ME; a ligand of Formula (II)

The phosphonate ester (potassium salt) from Example 2 was passed through a cation exchange column (Dowex™-50 X4-400) which had been conditioned with 1N HCl. After freeze drying of the aqueous eluent, the free acid was obtained as a floculant, snow white powder.

COMPLEX PREPARATION
General Procedure
Complex Preparation (for Biodistribution)

A stock $^{153}SmCl_3$ solution was prepared by adding 2 μL of $3\times10^{-4}M$ $^{153}SmCl_3$ in 0.1N HCl to 2 mL of a $3\times10^{-4}M$ $^{153}SmCl_3$ carrier solution in 0.1N HCl. The 1:1 ligand:metal complex was then prepared by combining 0.5 mL of ligand solution ($1.2\times10^{-3}$) with 2.0 mL of the stock metal, followed by thorough mixing, to give an acidic solution (pH=2). The pH was then adjusted to 7.5 using 0.1N NaOH to facilitate completion of complexation. The percent metal as complex was then determined by passing an aliquot of the complex solution through a Sephadex™ C-25 (cation exchange) column eluting with 4:1 saline (0.85% NaCl:$NH_4OH$) and collecting 2 mL fractions. The amount of radioactivity in the combined elutions was then compared with that retained on the resin where the noncomplexed metal is retained. Complexation was then determined by this method to be greater than 98%.

Octanol:Water Partition

The purified $^{153}Sm$ complex (500 μL) was combined with an equal volume of octanol. The two phases were then vigoursly agitated for one minute and the emulsion allowed to settle. A 100 μL aliquot was then removed from each phase and the partitioning coefficient determined from the amount of radioactivity detected in the different phases.

Complex Preparation (for Imaging Studies)

Metal ligand complexes were prepared by various methods. The methods included mixing of the metal and ligand in aqueous solution and adjusting the pH to the desired value. Complexation was done in solutions containing salts and/or buffers as well as water. Sometimes heated solutions were found to give higher complex yields than when the complexation was done at ambient temperatures.

The Gd-DOTP(F)ME complexes were formed by mixing $GdCl_3$ with a 5% stoichiometeric excess of ligand. A 0.1M $GdCl_3$ solution (1.0 mL), was mixed with 1.05 mL of a 0.1M ligand, then the sample was neutralized with KOH and diluted to 5.0 mL to make a 20 mL stock solution of complex.

Example 4

Preparation of the complex $^{153}$Sm-1,4,7,10-tetraazacyclododecane-1,4,7,10-tetra (methylenephosphonate monotrifluoromethyl ester)

The Sm-DOTP(F)ME complex was formed by preparing a solution of the ligand in deionized water (about pH 2). A ligand/metal complex was then prepared by combining the ligand solution with aqueous $SmCl_3$ ($3\times10^{-4}$ in 0.01N HCl) containing tracer $^{153}SmCl_3$. After thorough mixing, the percent metal as a complex was determined by passing a sample of the complex solution through a Sephadex™ column, eluting with 4:1 saline (0.85% NaCl/$NH_4OH$), and collecting 2×3 mL fractions. The amount of radioactivity in the combined elutions was then compared with that left on the resin. Under these conditions, complex was removed with the eluent and non-complexed metal is retained on the resin. By this method complexation was determined to be 95% or greater.

BIODISTRIBUTION
General Procedure
$^1H$ Relaxivity Measurements

Proton relaxivity, $r_1$, of Gd-DOTP(F)ME was determined as a function of $1/T_1$ vs. complex concentration [mM of Gd-DOTP(F)ME] at 40 MHz proton Lamor frequency at room temperature (about 25° C.). Concentration of 2.5 to 20 mM were examined.

Animal Biodistribution

Sprague Dawley rats were allowed to acclimate for five days then injected with 100 μL of the complex solution via a tail vein. The rats weighed between 150 and 200 g at the time of injection. After 30 min. the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ. The use of $^{159}Gd$ as radioactive tracer gave similar results.

The percent dose in blood was estimated assuming blood to be 6.5% of the body weight. The percent dose in bone was estimated by multiplying the percent dose in the femur by 25. The percent dose in muscle was estimated assuming muscle to be 43% of the body weight.

In addition to organ biodistribution, chelates of the compounds of Formula (II)–(VI) were evaluated for efficiency of bone localization since phosphonates are known for their ability to bind to hydroxyapatite.

Example I

The percent of the injected dose of complex of of Example 4 in several tissues are given in Table I. The numbers represent the average of a minimum of 3 rats per data point at 30 min and 2 hours post injection.

TABLE I

% INJECTED DOSE IN SEVERAL TISSUES FOR $^{153}$Sm-DOTP(F)ME

| Tissue | Average 30 min | Average 2 hr |
|---|---|---|
| Bone | 0.80 | 0.63 |
| Liver | 0.74 | 0.41 |
| Kidney | 0.38 | 0.23 |
| Spleen | 0.04 | 0.01 |
| Muscle | 0.60 | 0.53 |
| Blood | 0.27 | 0.03 |
| Heart | 0.01 | 0.01 |
| Lung | 0.04 | 0.05 |
| Brain | 0.01 | 0.01 |
| Stomach | 0.39 | 0.16 |
| Jejunum | 21.42 | 0.33 |
| Ileum | 72.26 | 94.43 |
| Large Intestine | 0.39 | 0.28 | each data point is the avarge of three rats

Figure 1:
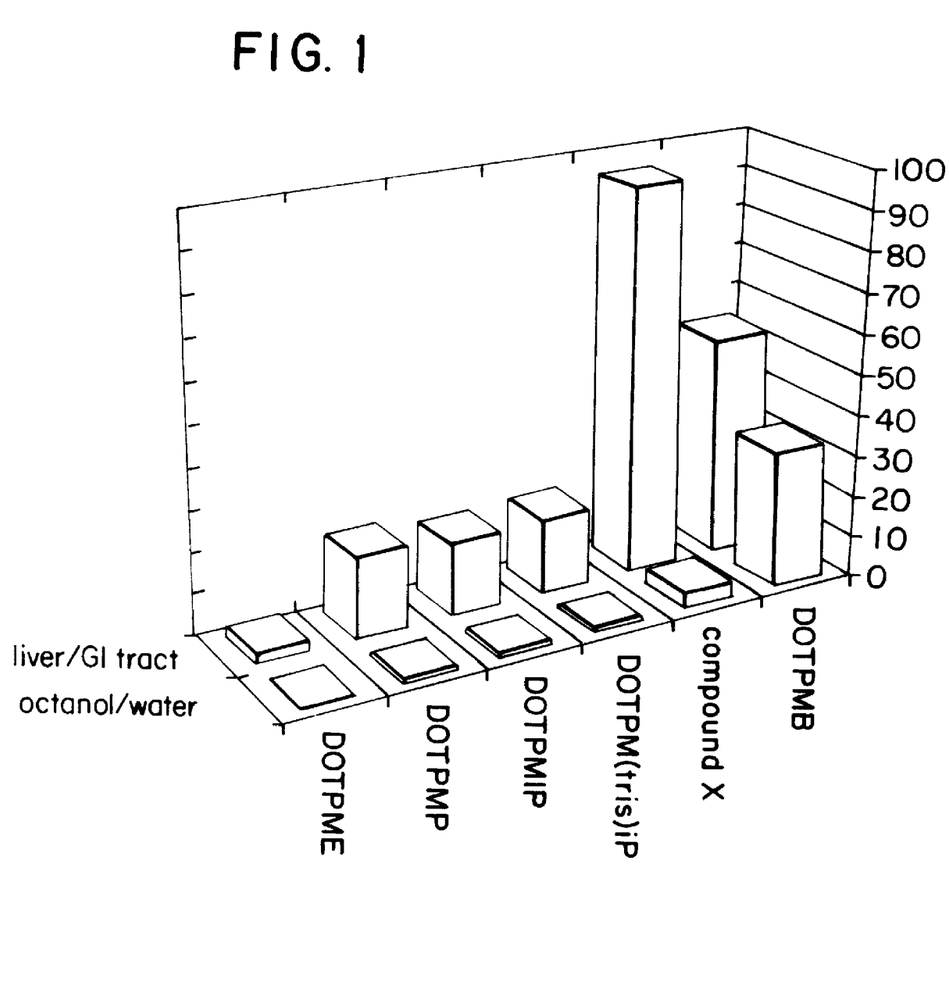
FIG. 1 shows the two hour biodistribution of liver contrast agents based on increasing octanol/water ratio.
Figure 2:
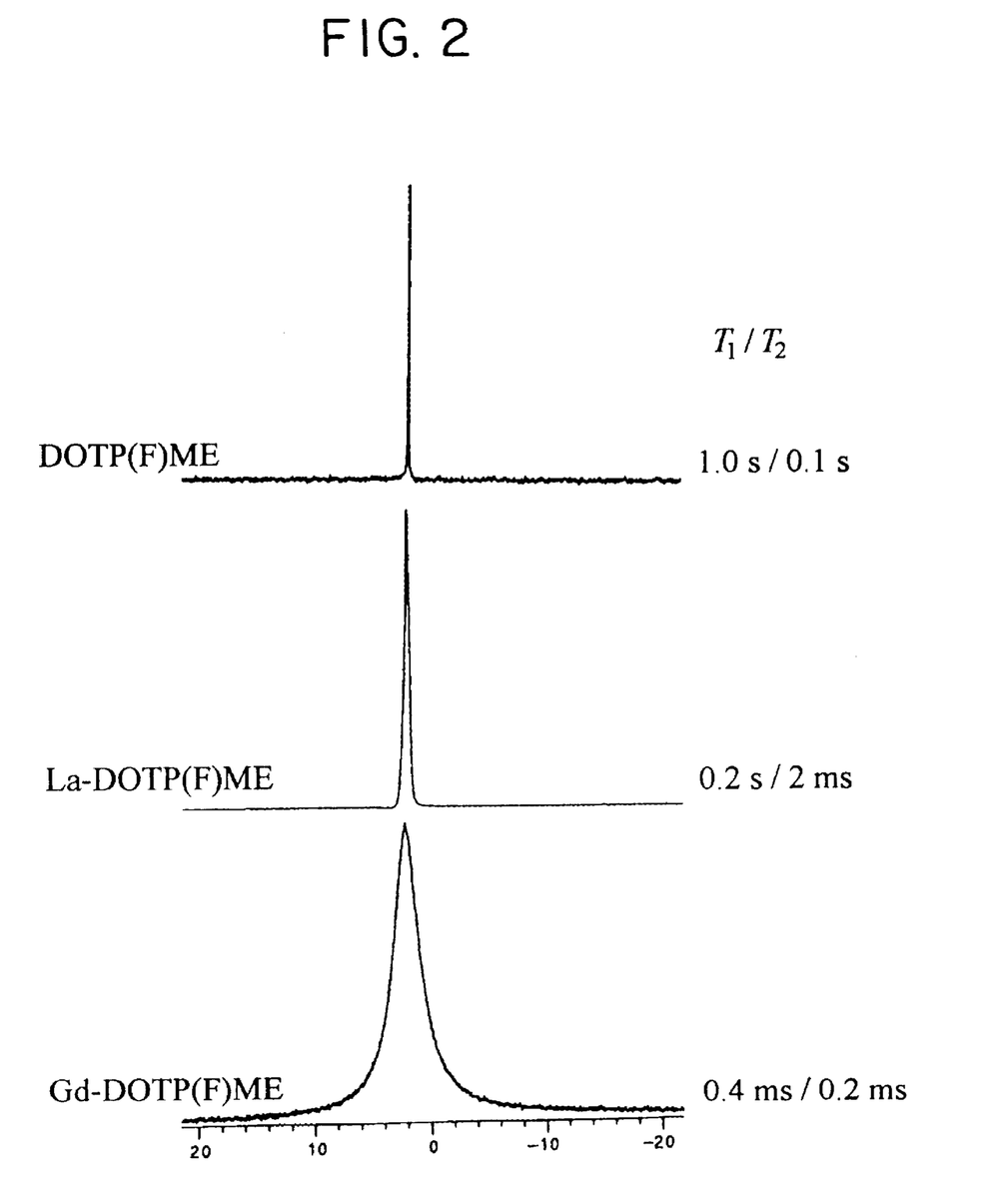
FIG. 2 shows $^{19}$F NMR spectra of the free ligand, DOTP(F)ME and its complexes with La$^{+3}$ and Gd$^{+3}$.
Figure 3A:
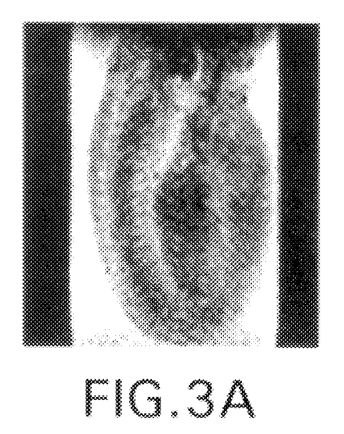
FIG. 3 shows images Nos. 1–6 of a $^{1}$H/$^{19}$F complex of this invention. Images 1–3 show a sagital slice through a perfused rat heart (arrested with KCl to avoid motion artifacts) under varying described conditions. Image 4 shows the same heart axial. Images 5 and 6 show gradient echo $^{19}$F images of a rat heart.
Figure 3B:
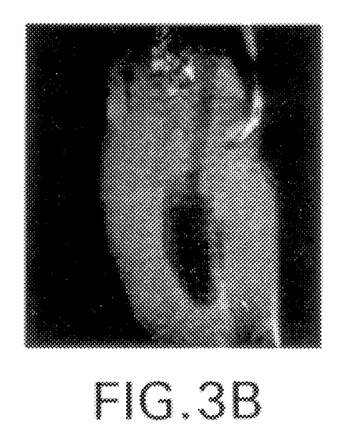
Figure 3C:
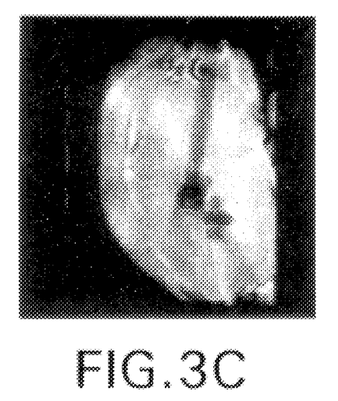
Figure 3D:
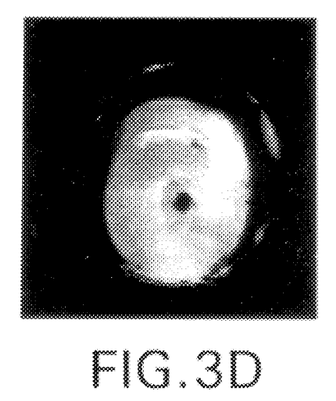
Figure 3E:
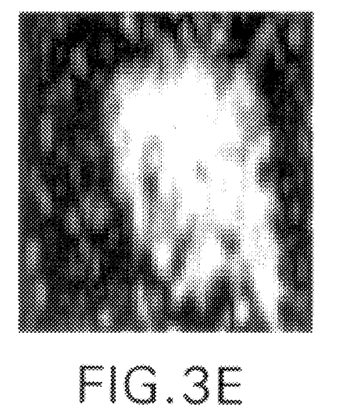
Figure 3F:
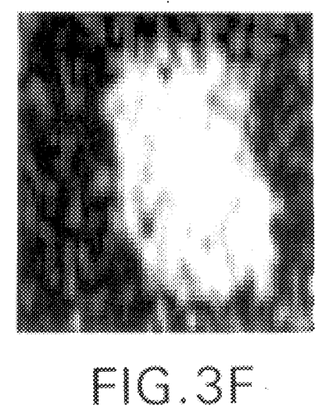

The liver contrast can been seen from FIG. 2 and the following Table II. Also it is apparent that the DOTP(F)ME ligand/complex has low lipophilicity.

TABLE II

Two Hour Biodistribution of Liver Contrast Agents Based on Increasing Octanol:Water Ratio Using $^{153}$Sm-ligand Complex

| Compound | Example No. | Octanol:-Water ratio | Liver/GI Tract | MW |
|---|---|---|---|---|
| DOTPME | E* | 0 | 3 | 813 |
| DOTPMP | E* | 0 | 20 | 869 |
| DOTPMiP | E* | 0 | 18 | 869 |
| DOTPM(tris)iP | E* | 0 | 18 | 695 |
| DOTP(F)ME | 2 & 3 | 4 | 95 | 1029 |
| DOTPMB | E* | 33 | 54 | 925 |
| PMBHE | E* | 78 | 31 | 771 |

*means prepared in a manner analogous to the indicated Example.

In Table II, the various compounds are:

DOTPME means 1,4,7,10-tetraazacyclododecane-1,4,7, 10-tetra(methylenephosphonate ethyl ester), and is a starting material for the ligands of the present invention.

DOTPMP means 1,4,7,10-tetraazacyclododecane-1,4,7, 10-tetra(methylenephosphonate n-propyl ester), and is a starting material for the ligands of the present invention.

DOTPMiP means 1,4,7,10-tetraazacyclododecane-1,4,7, 10-tetra(methylenephosphonate iso-propyl ester), and is a starting material for the ligands of the present invention.

DOTPM(tris)iP means 1,4,7,10-tetraazacyclododecane-1, 4,7-tris(methylenephosphonate iso-propyl ester), and is a starting material for the ligands of the present invention.

DOTPMB means 1,4,7,10-tetraazacyclododecane-1,4,7, 10-tetra(methylenephosphonate n-butyl ester), and is a starting material for the ligands of the present invention.

PMBHE means 3,6,9,15-tetraazabicyclo[9.3.1]-pentadeca-1(15),11,13-triene-3,6,9-methylene(n-butyl) phosphonate, and is a starting material for the ligands of the present invention.

As lipophilicity gradually increases (octanol/water ratio increases), one would expect a corresponding enhancement of intramolecular interactions between the chelate and lipophilic blood proteins upon intravenous injection. Thus, one would predict prolonged retention of the chelate in the blood pool and a corresponding increase in liver uptake and excretion through the gastrointestinal tract (GI). As expected, the highly lipophilic butyl ester displayed substantial liver uptake (33%) and rapid transport into the GI tract. Suprisingly, the fluoro ester displayed an even greater degree of liver uptake (95%), suggesting an alternate mechanism for hepatocyte recognition or possibly enhanced interactions with a specific protein. Thus the fluoro nucleus appears to have a unique influence on chelate biodistribution beyond what can be explained on the basis of lipophilic properties.

In general low molecular weight chelates with minimal lipophilic character are expected to be excreted from the body via glomerular filtration by the kidneys. Accordingly, all chelates through the propyl chain were found to have rapid and complete uptake by the kidneys and elimination through the urine.

Example II $^1$H and $^{19}$F NMR Spectra

The free ligand, DOTP(F)ME from Example 2, and its complexes with La$^{+3}$ and Gd$^{+3}$ are shown in FIG. 2. The signal from the free ligand (Example 2) is quite sharp with a line width of 3 Hz. Upon complexation with Gd$^{+3}$ (the paramagnetic metal used for proton imaging), the $^{19}$F line width broadens to about 1600 Hz. In this instance, line width should correlate closely to the actual relaxation parameters (T1 and T2) because the effects of paramagnetic relaxation by Gd$^{+3}$ dominates any small differences in chemical shifts of the CF$_3$ groups in the complex. The overall effect of this substantial line broadening is to dramatically reduce the $^{19}$F T2. In fact the T2 of this complex is so short that the signal decays too quickly for detection even at the shortest TE settings possible on the imaging system (about 1 ms). Attempts at obtaining $^{19}$F images using the Gd[DOTP(F) ME] complex were unsuccessful because of considerable $^{19}$F signal line broadening.

The line width of the $^{19}$F signal in the diamagnetic La$^{+3}$[DOTP(F)ME] complex is broader than anticipated based upon the rotational correlation time of this low molecular chelate. Spectra of some of the other paramagnetic lanthanide complexes show in fact that the CF$_3$ groups are not magnetically equivalent due to the introduction of multiple asymmetric centers at the phosphorous atom. Therefore, in this complex line width broadening is attributable to non-equivalent fluoromethyl signals. Furthermore, and importantly, since line broadening is an order of magnitude less than the paramagnetic complex, $^{19}$F imaging should be possible since T2 will be longer and within the working limits of the imaging system.

It appears likely that the alkyl chain length in the phosphonate ester can position the CF$_3$ moieties in magnetically equivalent environments and produce a Gd$^{+3}$ complex possessing a T2 long enough to generate adequate 19F images over a relatively short time period (minutes). Furthermore, combinations of other Ln$^{+3}$ cations possessing different relaxation properties with ligand variations where the placement of the CF3 groups has been altered, should also produce chelates capable of enhancing both proton and fluorine images.

IMAGING EXPERIMENTS

General Procedure

Injectable solutions were first prepared (0.5M) by dissolving the appropriate amount of each complex in 2 mL of deionized water. The pH of the solutions were then adjusted to 7.4 using 1M HCl or NaOH as needed. The total Gd content of each solution was then determined by ICP analysis.

An anesthetized Sprague Dawley rat was injected intramuscularly with one of the metal solutions described above at a dose of 0.05–0.1 mmol Gd/kg body weight. Images were then taken at various time intervals and compared with a non-injected control at time 0.

Example III

The Gd complex (prepared similar to Example 4) showed jejunum and ileum enhancement and bone localization in the shoulder, spine and sternum.

Example IV

Several examples of $^1$H and $^{19}$F images are shown in FIG. 3. Images #1–#4 are $^1$H images using Gd[DOTP(F)ME]. Images 5 and 6 are $^{19}$F images using La[DOTP(F)ME]. Image #1 shows a sagital slice through a perfused rat heart (arrested with KCl to avoid motion artifacts) suspended in the center of a 20 mm NMR tube. This $^1$H image was obtained on a 9.4T imaging/spectroscopy system using a TE (echo line) of 20 milliseconds (ms) and a TR (repetition line) of 500 ms. Image #2 wascollected after a line was positioned near the bottom of the NMR tube to remove excess perfusate from arround the heart. The dark object in the center of the heart is a balloon attached to a catheter filled with non-flowing perfusate used to monitor heart function (i.e., rate and pressure). Images #3 (sagital) and #4 (axial) show the same heart after 2 mM Gd[DOTP(F)ME] was added to the recirculating perfusate (TE=13.4 ms). Most of the heart shows enhanced $^1$H contrast indicating that this complexed agent enters all extracellular space. The coronary arteries appear to be enhanced even more because the concentration of the complexed agent in the vascular space was higher than the interstitial space when this image was collected.

Images #5 and #6 show three deminational gradient echo 19F images of a rat heart using TE=3 ms, TR=800 ms and TE=1.6 ms, TR=700 ms, respectively, using the La[DOTP(F)ME] chelate. Both images show that the complexed agent accesses all extracellular space as higher concentration of the complexed agent are seen in the ventricles.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A polyazamacrocyclofluoromonoalkylphosphonic acid compound of the formula:

wherein:

R is hydrogen or where:

m is 0 or an integer of 1 through 4;

n is an integer of 1, 2 or 3;

$R^1$ and $R^1$ are independently hydrogen or fluoro atom;

with the proviso that at least one R must be other than hydrogen;

Z is a group of the formula where R is defined as before;

q is an integer of 1 or 2;

y is an integer of 1, 2 or 3;

x is 0 or 1;

with the proviso that when y is 1, x is 1 and when y is 3, x is 0; or pharmaceutically-acceptable salts thereof.

2. A compound of claim 1 which is any one of the following formulae:

(II)

(III)

(IV)

-continued (V)

(VI)

wherein:

R is hydrogen or where:
m is 0 or an integer of 1 through 4;
n is an integer of 1, 2 or 3;
$R^1$ and $R^1$ are independently hydrogen or fluoro atom;
with the proviso that at least one R must be other than hydrogen; or
pharmaceutically-acceptable salts thereof.

3. A compound of claim 1 wherein all R terms are a fluoro moiety.

4. A compound of claim 1 wherein the compound is of Formula (II).

5. The compound of claim 4 which is 1,4,7,10-tetraazacyclododecane-1,4,7,10-tetra (methylenephosphonate monotrifluoroethyl ester), or its pharmaceutically-acceptable salts.

6. A complex which comprises a polyazamacrocyclofluoromonoalkylphosphonic acid compound of the formula:

(I)

wherein:

R is hydrogen or where:
m is 0 or an integer of 1 through 4;
n is an integer of 1, 2 or 3;
$R^1$ and $R^1$ are independently hydrogen or fluoro atom;
with the proviso that at least one R must be other than hydrogen;

Z is a group of the formula where R is defined as before;
q is an integer of 1 or 2;
y is an integer of 1, 2 or 3;
x is 0 or 1;
with the proviso that when y is 1, x is 1 and when y is 3, x is 0; or pharmaceutically-acceptable salts thereof;

complexed with a metal ion selected from the group consisting of $Gd^{+3}$, $Fe^{+3}$, $Mn^{+3}$, $Cr^{+3}$, $La^{+3}$, $Ce^{+3}$, $Pr^{+3}$, $Nd^{+3}$, $Pm^{+3}$, $Sm^{+3}$, $Eu^{+3}$, $Tb^{+3}$, $Dy^{+3}$, $Ho^{+3}$, $Er^{+3}$, $Tm^{+3}$, $Yb^{+3}$ and $Lu^{+3}$.

7. A complex of claim 6 wherein the polyazamacrocyclofluoromonoalkylphosphonic acid compound is any one of the following formulae:

(II)

(III)

(IV)

(V)

-continued (VI)

wherein:

R is hydrogen or where:
m is 0 or an integer of 1 through 4;
n is an integer of 1, 2 or 3;
$R^1$ and $R^1$ are independently hydrogen or fluoro atom;
with the proviso that at least one R must be other than hydrogen; or
pharmaceutically-acceptable salts thereof.

8. A complex of claim 7 wherein the metal ion is $La^{+3}$.

9. A complex of claim 7 wherein the metal ion is $Gd^{+3}$.

10. A complex of claim 7 wherein the compound is of Formula (II).

11. The complex of claim 10 wherein the compound is 1,4,7,10-tetraazacyclododecane-1,4,7,10-tetra (methylenephosphonate monotrifluoroethyl ester), or its pharmaceutically-acceptable salts, complexed with $Gd^{+3}$.

12. The complex of claim 10 wherein the compound is 1,4,7,10-tetraazacyclododecane-1,4,7,10-tetra (methylenephosphonate monotrifluoroethyl ester), or its pharmaceutically-acceptable salts, complexed with $La^{+3}$.

13. A pharmaceutical formulation comprising a complex of claim 6 with a pharmaceutically-acceptable carrier.

14. A pharmaceutical formulation comprising a complex of claim 7 with a pharmaceutically-acceptable carrier.

15. A pharmaceutical formulation comprising a complex of claim 10 with a pharmaceutically-acceptable carrier.

16. A pharmaceutical formulation comprising a complex of claim 11 with a pharmaceutically-acceptable carrier.

17. A pharmaceutical formulation comprising a complex of claim 12 with a pharmaceutically-acceptable carrier.

18. A method for diagnosis in an animal which comprises administering to said animal an effective amount of the formulation of claim 6.

19. A method for diagnosis in an animal which comprises administering to said animal an effective amount of the formulation of claim 7.

20. A method for diagnosis in an animal which comprises administering to said animal an effective amount of the formulation of claim 10.

21. A method for diagnosis in an animal which comprises administering to said animal an effective amount of the formulation of claim 11.

22. A method for diagnosis in an animal which comprises administering to said animal an effective amount of the formulation of claim 12.

* * * * *